United States Patent
Wang

(10) Patent No.: US 10,034,957 B2
(45) Date of Patent: Jul. 31, 2018

(54) COMPACTED HEMOSTATIC CELLULOSIC AGGREGATES

(71) Applicant: Ethicon, Inc., Somerville, NJ (US)

(72) Inventor: Yi-Lan Wang, Somerset, NJ (US)

(73) Assignee: Ethicon LLC, Guaynabo, PR (US)

(*) Notice: Subject to any disclaimer, the term of this patent is extended or adjusted under 35 U.S.C. 154(b) by 0 days.

(21) Appl. No.: 15/337,337

(22) Filed: Oct. 28, 2016

(65) Prior Publication Data
US 2017/0128618 A1  May 11, 2017

Related U.S. Application Data

(60) Provisional application No. 62/251,773, filed on Nov. 6, 2015, provisional application No. 62/371,954, filed on Aug. 8, 2016, provisional application No. 62/408,176, filed on Oct. 14, 2016.

(51) Int. Cl.
*A61L 26/00* (2006.01)
*D01D 5/42* (2006.01)

(52) U.S. Cl.
CPC ....... *A61L 26/0023* (2013.01); *A61L 26/0061* (2013.01); *D01D 5/426* (2013.01); *A61L 2400/04* (2013.01)

(58) Field of Classification Search
CPC ............... A61K 9/1652; A61L 26/0023; A61L 26/0061; A61L 2400/04; D01D 5/426
See application file for complete search history.

(56) References Cited

U.S. PATENT DOCUMENTS

| | | | |
|---|---|---|---|
| 3,364,200 A | 11/1961 | Ashton et al. |
| 4,626,253 A | 12/1986 | Broadnax, Jr. |
| 5,180,398 A | 1/1993 | Boardman et al. |
| 5,484,913 A | 1/1996 | Stilwell et al. |
| 5,645,849 A | 7/1997 | Pruss et al. |

(Continued)

FOREIGN PATENT DOCUMENTS

| | | |
|---|---|---|
| CN | 101716383 | 6/2010 |
| CN | 104721878 | 4/2015 |

(Continued)

OTHER PUBLICATIONS

International Search Report re: PCT/US2016/059429 dated Feb. 28, 2017.

(Continued)

*Primary Examiner* — Michael B. Pallay
(74) *Attorney, Agent, or Firm* — David R. Crichton; Leo Kriksunov

(57) ABSTRACT

The present invention is directed to a hemostatic material comprising a compacted, hemostatic aggregates of cellulosic fibers. In some aspects, the hemostatic material further includes additives, such as carboxymethyl cellulose (CMC) or other polysaccharides, calcium salts, anti-infective agents, hemostasis promoting agents, gelatin, collagen, or combinations thereof. In another aspect, the present invention is directed to a method of making the hemostatic materials described above by compacting a cellulosic-based material into hemostatic aggregates. In another aspect, the present invention is directed to a method of treating a wound by applying hemostatic materials described above onto and/or into the wound of a patient.

14 Claims, 7 Drawing Sheets

(56) References Cited

U.S. PATENT DOCUMENTS

| | | |
|---|---|---|
| 5,696,191 A | 12/1997 | Nohr et al. |
| 6,162,241 A | 12/2000 | Coury et al. |
| 6,177,126 B1 | 1/2001 | Hagedorn et al. |
| 6,200,587 B1 | 3/2001 | Soe et al. |
| 6,225,461 B1 | 5/2001 | Akimoto et al. |
| 6,309,454 B1 | 10/2001 | Harvey et al. |
| 6,596,318 B2 | 7/2003 | Prasch et al. |
| 6,627,749 B1 | 9/2003 | Kumar |
| 6,733,774 B2 | 5/2004 | Stimmeder |
| 6,762,336 B1 | 7/2004 | MacPhee et al. |
| 7,052,713 B2 | 5/2006 | Stimmeder |
| 7,094,428 B2 | 8/2006 | Spillert et al. |
| 7,189,410 B1 | 3/2007 | Drohan et al. |
| 7,351,422 B2 | 4/2008 | Jo et al. |
| 7,666,803 B2 | 2/2010 | Shetty et al. |
| 8,815,832 B2 | 8/2014 | Wang et al. |
| 8,840,877 B2 | 9/2014 | Adamson et al. |
| 8,846,105 B2 | 9/2014 | Koopman et al. |
| 9,717,821 B2 | 8/2017 | Schutte et al. |
| 9,724,213 B2 | 8/2017 | Zhang et al. |
| 9,795,773 B2 | 10/2017 | Boyes et al. |
| 2004/0005350 A1 | 1/2004 | Looney et al. |
| 2006/0088589 A1 | 4/2006 | Gorman et al. |
| 2006/0159733 A1 | 7/2006 | Pendharkar et al. |
| 2006/0233869 A1 | 10/2006 | Looney et al. |
| 2008/0027365 A1 | 1/2008 | Huey |
| 2010/0119563 A1 | 5/2010 | Miyagawa et al. |
| 2013/0316974 A1* | 11/2013 | Wang .................. A61L 26/009 514/57 |
| 2014/0369991 A1 | 12/2014 | Schutte et al. |
| 2016/0015792 A1 | 1/2016 | Hendricus Van Pinxteren et al. |

FOREIGN PATENT DOCUMENTS

| | | |
|---|---|---|
| EP | 1323436 | 7/2003 |
| EP | 918548 | 8/2003 |
| EP | 1493451 | 9/2010 |
| EP | 1809343 | 8/2012 |
| KR | 804434 | 2/2008 |
| KR | 2014-0086072 | 7/2014 |
| KR | 1588633 | 1/2016 |
| KR | 1624625 | 5/2016 |
| RU | 2235539 | 9/2004 |
| WO | WO 2001/024841 | 4/2001 |
| WO | WO 2004/064878 | 8/2004 |
| WO | WO 2007/076415 | 7/2007 |
| WO | WO 2014/135689 | 9/2014 |

OTHER PUBLICATIONS

Written Opinion re: PCT/US2016/059429 dated Feb. 28, 2017.

Cullen, B. et al "The role of oxidized regenerated cellulose/collagen in chronic wound repair and its potential mechanism of action" The International Journal of Biochemistry & Cell Biology (2002) 34 pp. 1544-1556.

Howsmon, J.A. et al "The Ball-Milling of Cellulose Fibers and Recrystallization Effects" Journal of Applied Polymer Science (1959) vol. 1, Issue 3, pp. 313-322.

Rajkhowa, R. et al. Ultra-fine silk powders powder preparation through rotary and ball milling Powder Technology (2008)185 pp. 87-95.

Yasnitskii, B.G. et al., 'Oxycelodex, a new hemostatic preparation' Pharmaceutical Chemistry Journal (1983) vol. 18, No. 4, pp. 506-508 (Abstract 2 pages).

International Search Report re: PCT/IB2017/054884 dated Dec. 1, 2017.

Written Opinion re: PCT/IB2017/054884 dated Dec. 1, 2017.

U.S. Appl. No. 62/251,773, filed Nov. 6, 2015.

\* cited by examiner

COMPACTED HEMOSTATIC CELLULOSIC AGGREGATES

FIELD OF THE INVENTION

The present invention is directed to flowable, bioresorbable hemostatic materials, particularly compacted aggregates of cellulose fibers, and to methods for manufacturing such materials.

BACKGROUND OF THE INVENTION

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

Bleeding during surgical procedures may manifest in many forms. It can be discrete or diffuse from a large surface area. It can be from large or small vessels, arterial (high pressure) or venous (low pressure) of high or low volume. It may be easily accessible or it may originate from difficult to access sites.

Conventional methods to achieve hemostasis include use of surgical techniques, sutures, ligatures or clips, and energy-based coagulation or cauterization. When these conventional measures are ineffective or impractical, adjunctive hemostasis techniques and products are typically utilized.

The selection of appropriate methods or products for the control of bleeding is dependent upon many factors, which include but are not limited to bleeding severity, anatomical location of the source and the proximity of adjacent critical structures, whether the bleeding is from a discrete source or from a broader surface area, visibility and precise identification of the source and access to the source.

In an effort to address the above-described problems, materials have been developed for controlling excessive bleeding. Topical Absorbable Hemostats (TAHs) are widely used in surgical applications. TAHs encompass products based on oxidized cellulose (OC), oxidized regenerated cellulose (ORC), gelatin, collagen, chitin, chitosan, etc. To improve the hemostatic performance, scaffolds based on the above materials can be combined with biologically-derived clotting factors, such as thrombin and fibrinogen.

Many products have been developed as adjuncts to hemostasis. These products include topical absorbable hemostats (TAH) such as oxidized regenerated cellulose, gelatin in various forms with or without a thrombin solution, and collagen powder, as well as biologically active topical hemostatic products (topical thrombin solutions, fibrin sealants, etc.) and a variety of synthetic topical sealants.

One of the most commonly used topical hemostatic agents is SURGICEL® Original absorbable hemostat, made from oxidized regenerated cellulose (ORC). ORC was introduced in 1960 as a safe and effective hemostatic agent for many surgical procedures. ORC fabric has a loose knit in its matrix structure and conforms rapidly to its immediate surroundings and is easier to manage than other absorbable agents because it does not stick to surgical instruments and its size can be easily trimmed. This allows the surgeon to hold the cellulose firmly in place until all bleeding stops.

The control of bleeding is essential and critical in surgical procedures to minimize blood loss, to reduce post-surgical complications, and to shorten the duration of the surgery in the operating room. Due to its biodegradability and its bactericidal and hemostatic properties, oxidized cellulose, as well as oxidized regenerated cellulose has long been used as a topical hemostatic wound dressing in a variety of surgical procedures, including neurosurgery, abdominal surgery, cardiovascular surgery, thoracic surgery, head and neck surgery, pelvic surgery and skin and subcutaneous tissue procedures. A number of methods for forming various types of hemostats based on oxidized cellulose materials are known, whether made in powder, woven, non-woven, knit, and other forms. Currently utilized hemostatic wound dressings include knitted or non-woven fabrics comprising oxidized regenerated cellulose (ORC), which is oxidized cellulose with increased homogeneity of the cellulose fiber.

SURGICEL® absorbable hemostats are used adjunctively in surgical procedures to assist in the control of capillary, venous, and small arterial hemorrhage when ligation or other conventional methods of control are impractical or ineffective. The SURGICEL® family of absorbable hemostats consists of four main product groups, with all hemostatic wound dressings commercially available from Ethicon, Inc., Somerville, N.J., a Johnson & Johnson Company: SURGICEL® Original hemostat is a white fabric with a pale yellow cast and a faint, caramel like aroma, this material is strong and can be sutured or cut without fraying; SURGICEL® NU-KNIT® absorbable hemostat is similar to Original but has a denser knit and thus a higher tensile strength, this material is particularly recommended for use in trauma and transplant surgery as it can be wrapped or sutured in place to control bleeding; SURGICEL® FIBRILLAR™ absorbable hemostat form of the product has a layered structure that allows the surgeon to peel off and grasp with forceps any amount of material needed to achieve hemostasis at a particular bleeding site, may be more convenient than the knitted form for hard to reach or irregularly shaped bleeding sites and is particularly recommended for use in orthopedic/spine and neurological surgery; SURGICEL® SNoW™ absorbable hemostat form of the product is a structured non-woven fabric that may be more convenient than other forms for endoscopic use due to the structured, non-woven fabric and is highly adaptable and recommended in both open and minimally invasive procedures.

Other examples of commercial resorbable hemostats containing oxidized cellulose include GelitaCel® resorbable cellulose surgical dressing from Gelita Medical BV, Amsterdam, The Netherlands. The commercially available oxidized cellulose hemostats noted above are available in knitted, nonwoven fabrics or powder form. Additional hemostatic products, such as powders consisting of microporous polysaccharide particles and plant starch based particles, are also commercially available as Arista and Perclot.

U.S. Pat. No. 8,815,832 discloses a hemostatic material comprising a ball milled compacted ORC powder comprising particles having average aspect ratio from about 1 to about 18, said powder having tapped density of at least 0.45 g/cm$^3$, an average size of 1.75 microns to 116 microns with a median size of 36 microns and a flowability of at least 7.5 cm/s.

U.S. Pat. No. 3,364,200 to Ashton and Moser describes a resorbable, surgical hemostat in the form of pledgets of integrated oxidized cellulose staple fibers.

U.S. Patent Publication 2008/0027365 to Huey describes an apparatus for promoting hemostasis utilizing oxidized cellulose in the form of a compressible, shapeable mass that is formed into a sheet for placement on a bleed site and further having a sleeve in a form of a tubular shell dimensioned to receive a limb.

U.S. Patent Publication 2004/0005350 to Looney et al. discloses hemostatic wound dressings utilizing a fibrous fabric substrate made from carboxylic-oxidized cellulose and containing a porous, polymeric matrix homogeneously distributed through the fabric and made of a biocompatible, water-soluble or water-swellable cellulose polymer, wherein the fabric contains about 3 percent by weight or more of water-soluble oligosaccharides.

PCT Patent Publication WO 2007/076415 by Herzberg et al. and entitled "COMPOSITIONS AND METHODS FOR PREVENTING OR REDUCING POSTOPERATIVE ILEUS AND GASTRIC STASIS", discloses milling of ORC, particularly cryogenic milling, using a cutting blade of a motor-driven mill.

An article titled "The Ball-Milling of Cellulose Fibers and Recrystallization Effects", Journal of Applied Polymer Science, Volume 1 Issue 3, Pages 313-322, (1959) by Howsmon and Marchessault, reports results of a study of the effect of fine structure on the decrystallization process which results from the ball-milling of cellulose. The rate of decrystallization is sensitive to the type of fine structure and is accelerated by the presence of moisture. The extent of chain degradation was greater in air atmosphere than in carbon dioxide, suggesting that mechanically induced free radical degradation occurs along with other chain-breaking processes. A study of the density and moisture regain of the samples after various times of milling showed that a linear relation between regain and density held over the entire range studied. The relation was the same for native and regenerated cellulose. The process of recrystallization of the ball-milled samples was studied under various conditions and compared to the hydrolytically induced recrystallization of rayons. The reference discloses effect of fine structure on the decrystallization process which results from the ball-milling of cellulose fibers.

U.S. Pat. No. 6,627,749 discloses a process for grinding oxidized cellulose using a pestle and mortar or in a ball mill or any other conventional laboratory grinder. It further discloses that when cotton linter sheet is used as the starting cellulose source, the fiber length of the product decreases with increasing reaction time. When ball-milled, the long fibrous structures of the product turn into smaller fibers, to loosely-packed spherical aggregates. No significant change in the crystallinity of these samples occurs as a result of ball milling. The reference discloses long fibrous oxidized cellulose ball milled to form small fibers or loosely packed spherical aggregates.

Other related references include: U.S. Pat. No. 6,309,454, "Freeze-dried composite materials and processes for the production thereof"; U.S. Pat. Nos. 5,696,191; 6,627,749; 6,225,461 to Kyoko et al.; PCT Patent Publication WO2001/024841 A1, Compositions for the Treatment of Wound Contracture; and European patent publication EP1,323,436 to Dae Sik et al.

Other related references include: An article titled "The role of oxidized regenerated cellulose/collagen in chronic wound repair and its potential mechanism of action", The International Journal of Biochemistry & Cell Biology 34 (2002) 1544-1556, Breda Cullen et al.; an article by Rangam et al. teaching methods of making silk powders through milling processes [Powder Technology 185 (2008), p 87-95]; an article by Yasnitskii et al., Oxycelodex, a new hemostatic preparation, Pharmaceutical Chemistry Journal, 18, 506-508; discloses an Oxycelodex paste that consists of two components, oxidized cellulose powder and a 20% aqueous solution of dextran.

U.S. Patent Publication 2006/0233869 to Looney et al. discloses using a chopping or shredding process to make ORC micro-fibers from ORC fabrics. The rod-like shaped fibers had sizes which ranged from about 35 to 4350 micrometers.

There is a need in improved hemostatic forms and materials which facilitate ease of application and rapid onset of hemostasis.

SUMMARY OF THE INVENTION

The present invention is directed to a hemostatic material comprising a compacted, hemostatic aggregates of cellulosic fibers. In some aspects, the hemostatic material further includes additives, such as carboxymethyl cellulose (CMC) or other polysaccharides, calcium salts, anti-infective agents, hemostasis promoting agents, gelatin, collagen, or combinations thereof. In another aspect, the present invention is directed to a method of making the hemostatic materials described above by compacting a cellulosic-based material into hemostatic aggregates. In another aspect, the present invention is directed to a method of treating a wound by applying hemostatic materials described above onto and/or into the wound of a patient.

The present invention is also directed to method of making a plurality of hemostatic aggregates milling a cellulosic source material to form an intermediate fine fibers; humidifying the intermediate fine fibers; roller compacting the intermediate fine fibers to form hemostatic aggregates; sieving the hemostatic aggregates; dehumidifying the hemostatic aggregates; and optionally dosing the resulting hemostatic aggregates into storage containers or into delivery devices. The milling step can be preceded by a step of slitting and cutting the cellulosic source material forming pieces. The milling step can be a two-part process with the second part is performed in an air classifier wherein the second part can be repeated three times. The intermediate fine fiber preferably has a size distribution with d50 of less than about 100 microns and d90 of less than about 180 microns. The intermediate fine fibers can be humidified to water content of between 11.0% and 20% by weight. The intermediate fine fibers can be roller compacted material and then subjected to pre-breaking and subsequently followed by a step of final milling. The intermediate fine fibers are preferably compacted at a roller pressure of at least 130 bars. The intermediate fine fibers are preferably compacted at a roller force of at least 26.0 kN/cm. The resulting materials are selected to produce a targeted hemostatic aggregates fraction having dimensions along their longest axis of 75-300 μm by screen sieving method. Preferably, the targeted hemostatic aggregates fraction is characterized by a size distribution such that d15 is greater than about 80 microns, d50 is from about 140 to 250 microns and d90 is less than about 370 microns. The hemostatic aggregates intended for dosing preferably having a moisture content of loss on drying of less than about 5%, more preferably less than 2%. The source materials can be selected from oxidized regenerated cellulosic fabric, oxidized regenerated cellulose non-woven fabric, shredded oxidized regenerated cellulosic material or combinations thereof. The source materials can further comprises an additive selected from the group consisting of carboxymethyl cellulose, calcium salt, an anti-infective agent, a hemostasis promoting agent, gelatin, collagen, or combinations thereof. The present invention further relates to a method of treating a wound by applying the hemostatic aggregates prepared as described above onto and/or into the wound of a patient.

The present invention further relates to hemostatic particulate aggregates composed of a plurality of interconnected individual cellulosic fibrils that in aggregate form have a sphericity of at least 0.5, a diameter along its longest axis that is less than about 500 microns and greater than about 50 microns. The hemostatic aggregates can alternatively be expressed as having a size distribution profile with d15 greater than about 80 microns, d50 from about 140 to 250 microns, d90 less than about 370 microns, a bulk density greater than 0.45 g/mL, and sphericity (sh50) equal or greater than 0.70. The hemostatic aggregate preferably are characterized by having substantially no size distribution changes or minimal size distribution changes when subjected to a vibratory challenge, more preferably the size distribution profile of the hemostatic aggregates as measured by d50 does not fall below 100 microns. In one embodiment, the size distribution changes are characterized by a QICPIC optical sensor at 0.2 bars. In a still further embodiment, the size distribution changes or minimal size distribution changes are based to processing at 1.0 bar vacuum.

The present invention further relates to hemostatic aggregates that have been milled, humidified, roller compacted, and dried cellulosic material. The present invention further relates to methods of treating a wound by applying the hemostatic aggregates as described above onto and/or into the wound of a patient.

DETAILED DESCRIPTION

Figure 1:
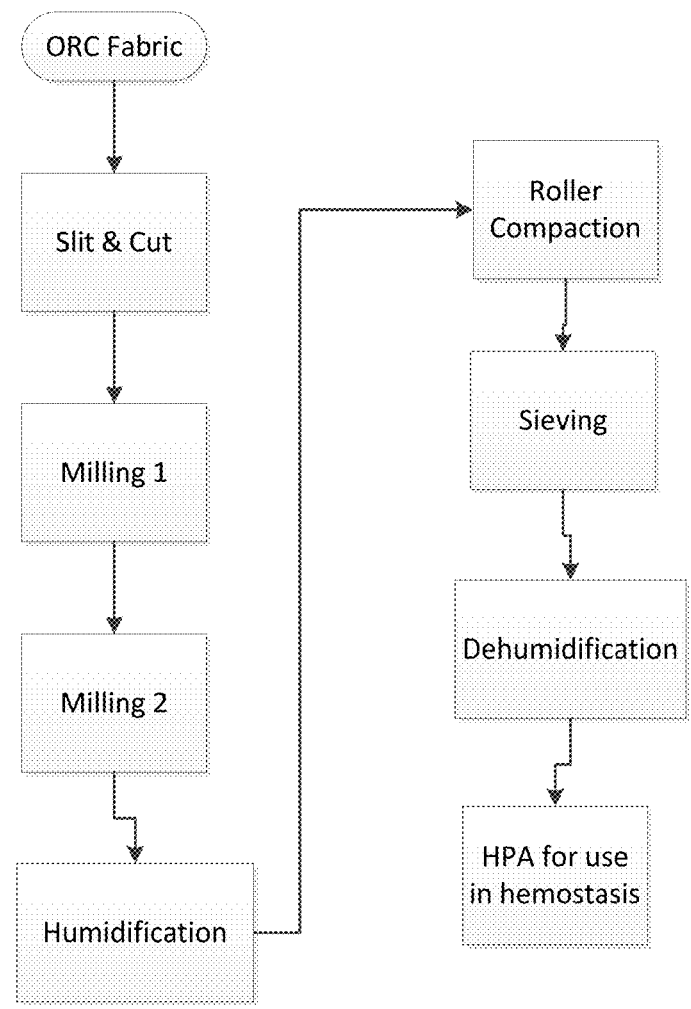
FIG. 1 is a schematic diagram of the manufacturing process.

The inventors discovered a process for making hemostatic aggregates having surprising properties and highly beneficial effects for hemostasis. Hemostatic aggregates according to the present invention are made from oxidized cellulose-based fiber materials or from pre-shredded oxidized cellulose-based materials, whereby the resulting hemostatic aggregates can be used for various surgical and wound healing topical applications, such as anti-adhesion barriers, hemostats, tissue sealants, etc. Oxidized regenerated cellulose materials that can be used as a starting material for making the hemostatic aggregates of the present invention are known and commercially available. The starting materials can include absorbable woven or knitted fabric or non-woven materials comprising oxidized polysaccharides, in particular oxidized cellulose and the neutralized derivatives thereof. For example, the cellulose may be carboxylic-oxidized or aldehyde-oxidized cellulose. More preferably, oxidized regenerated polysaccharides including, but without limitation, oxidized regenerated cellulose may be used. Oxidized regenerated cellulose is preferred due to its higher degree of uniformity versus cellulose that has not been regenerated. Regenerated cellulose and a detailed description of how to make oxidized regenerated cellulose are set forth in U.S. Pat. Nos. 3,364,200, 5,180,398 and 4,626,253, the contents of each of which are hereby incorporated by reference as if set forth in its entirety.

Examples of preferred cellulosic materials that may be utilized include, but are not limited to, INTERCEED® absorbable adhesion barrier, SURGICEL® Original absorbable hemostat, SURGICEL® NU-KNIT® absorbable hemostat, SURGICEL® FIBRILLAR™ absorbable hemostat, SURGICEL® SNoW™ absorbable hemostat.

Hemostatic aggregates of the present invention can perform as a hemostat in either a paste or powder form with superior hemostatic properties and good tissue conformability and flowability. In addition, hemostatic aggregates can be physically incorporated with other agents and biopolymers to improve adherence to tissues, sealing properties, and/or anti-adhesions properties.

In one aspect of the present invention, there is provided a method for making hemostatic aggregates having beneficial hemostatic, wound healing, and other therapeutic properties. A preferred method of the present invention is applied to manufacture hemostatic aggregates directly from cellulosic materials, such as ORC fabric or non-woven products such as these discussed above.

Briefly, a preferred manufacturing process starts with ORC material, such as SURGICEL® Original absorbable hemostat, as which is cut into 1- to 2-inch wide sections before the material is fed into a blade that cuts the fabric into smaller pieces. The cut ORC fabric pieces are then ground into intermediate ORC fine fibers by two consecutive milling processes (hammer milling and air classifier milling). In an alternative embodiment, the cut ORC fabric pieces are converted directly into intermediate fine fibers in a ball mill. The resulting intermediate ORC fine fibers are then humidified to about 11% to about 16% as measured by Ohaus halogen moisture analyzer and then roller compacted into larger aggregates. The moisture analyzer operates on a thermogravimetric principle wherein the moisture analyzer determines the weight of the sample; the sample is then quickly heated by the integral halogen dryer unit and moisture vaporizes. During the drying operation, the instrument continuously determines the weight of the sample and displays the result. On completion of drying, a tabulated result is displayed as percent moisture content, percent solids, weight or percent regain, in particular, the analyzer tests between 0.5-1 grams of aggregate with a four (4) minute ramp, 90 C maximum temperature and the following settings: Test ID—LOD; Profile—Standard; Dry Temperature—90 C; Switch Off—A60; Result—Moisture %; Custom—Off; Target Weight—None. Sieving is preferably done to separate target particles between the size of 75 and 300 microns determined by screen sieving.

Excess moisture introduced for purposes of compaction is removed by a dehumidification or drying process after compaction and sieving step for subsequent dosing into applicator devices and then subjected to the device packaging and sterilization. Preferred storage moisture prior to dosing into an applicator is preferably less than about 2% at conclusion of drying to achieve preferably less than 6% moisture content in controlled environment (0.3-0.6%/hr per 500 gram sample moisture gain depending on relative humidity, commonly 25-55% relative humidity) for dosing into applicators.

More specifically, one process for manufacturing the inventive hemostatic aggregates comprises the steps of: a) slitting and cutting of cellulosic source material; b) milling the resulting material from step a); c) a second milling step in an air classifier; d) humidification; e) roller compaction; f) sieving; g) dehumidification or drying; h) optional dosing into storage containers or into delivery devices, primary packaging and secondary packaging; and i) optional sterilization.

Slitting and cutting can preferably be performed to slit and cut fabric into appropriate size pieces that are between approximately 1 inch by 3 inches or 2 inches by 3 inches, though smaller pieces can also be used. The main operations performed for slitting and cutting are to unwind a roll of fabric, slit the fabric into strips, cut the strips to size and deliver the cut pieces into the first milling step. A number of cutting and slitting machines are known and commercially available, such as AZCO Model FTW-1000 available from AZCO.

In the first milling step, processed pieces of cellulosic fabric are converted from an intermediate coarse fiber produced in the slitting and cutting step to a material having a D90 value of less than 452 µm and D50 value of less than 218 µm, while having minimal impact on the color index and water soluble content of the material. A number of machines for milling are commercially available, such as Models DASO6 and WJ-RS-D6A manufactured by Fitzpatrick, which are hammer mill type milling machines, equipped with a 497 micron round screen and a set of blades that breaks down the fabric until it passes through the screen to produce intermediate coarse cellulosic fiber. In an exemplary processing run, mill speed can be about 7000 RPM; processing temperature at less than 80° C.; screen size between 1534 and 9004; number of blades as 8 (2 impellers each); blade type as a 225 knife, impact type blades; blade orientation set as "impact".

Size distribution D50 is also known as the median diameter or the medium value of the aggregate size distribution, it is the value of the aggregate's diameter at 50% in the cumulative distribution. For example, if D50 is 218 µm, then 50% of the aggregates in the sample are larger than 218 µm, and 50% are smaller than 218 µm. Size distribution is the number of aggregates that fall into each of the various size ranges given as a percentage of the total number of all sizes in the sample of interest. Accordingly, D90 value refers to 90% of aggregates having a size that is smaller than the D90 value, while D10 refers to 10% of aggregates having a size smaller than the D10 value.

At this stage in the preferred process, the size of the intermediate coarse fiber produced in the first milling step is further reduced to a D90 value of less than 177 µm and a D50 value of less than 95 µm while keeping a minimal impact on the color index and water soluble content of the material. A number of machines are available for second milling step, such as an Air Classifier/F10 Quadro Fine Grind from Quadro.

Intermediate coarse fiber from the first milling step can be fed at a controlled rate into the second mill and passed through two milling chambers that are separated by a milling screen. The material can be pulled through the milling chamber by an air blower. The intermediate coarse fiber can be processed through the air classifier equipment three times in order to obtain the desired size. At the end of the second milling step, the intermediate fine fiber can be collected.

In an exemplary processing run, a Quadro Air Classifier F10 can be used in the second milling step with a milling speed of 8400 rpm, blower speed of 1800 rpm, 0.0018" round hole screen and 3 passes. ORC intermediate fine fiber can be also produced in one step by ball milling instead of the two steps milling steps as described above. In an alternative ball milling embodiment, 50 g of pre-cut ORC fabric (2"×2") is ball milled with 12 high-density Zirconia (zirconium dioxide ZrO2, 20 mm in diameter; Glen Mills Inc., Clifton, N.J., USA) by placing the balls and the samples in a 500 mL grinding jar. The jar is clamped into the latching brackets and then counterbalanced on the planetary ball mill PM100; Retsch, Inc., Newtown, Pa., USA). The milling is then performed bi-directionally at 450 rpm for 20 minutes.

Following the milling process, the resulting cellulosic intermediate fine fiber is humidified to a moisture content between preferably about 11% and about 18%, more preferably between 11% and about 16%, most preferably about 12-16% for the subsequent processing, including a roller compaction process. A preferred humidity chamber suitable for the humidification step is commercially available as Model CEO-916-4-B-WF4-QS by Thermal Product Solutions. Humidification of chamber air is achieved by water vapor injection. The typical steady-state temperature of 25° C. can be utilized, while the humidity level can be cycled between 75% and 85%, with a preferred target of 85% air humidity. Humidification time or residence time of the material inside the humidity chamber can range from several hours to several days depending on the quantity of the material and air recirculation. In a typical and preferred cycle, the material will have 12-13 hours residence time for about 3,000 grams of cellulosic intermediate fine fiber arranged in several trays and exposed to 85% relative humidity and a target of 12% moisture content of the powder after humidification.

Use of cellulosic intermediate fine fiber with a moisture content fed into the compaction step that is greater than 16%, such as a moisture content of 20% by weight, the resulting ORC intermediate fine fiber caked during compaction, exhibited very poor flowability, and jammed the compactor. Thus, high humidity of the intermediate fine fiber does not result in suitable hemostatic aggregate materials. Conversely, when the moisture content of the intermediate fine cellulosic fiber is lower than about 8%, the yield of hemostatic aggregates is extremely low, somewhere about 5% yield of desired hemostatic aggregates.

Humidified intermediate fine ORC fiber is then compacted and sieved to obtain hemostatic aggregate materials. The roller compactor compacts the feed, which is then subjected to pre-breaking, final milling and sieving in a screener to obtain the desired hemostatic aggregates sizes.

Compaction equipment is known and commercially available. Exemplary compaction units are the Fitzpatrick Chilsonator IRR220-L1A with Retsch manual sieving AS200 Screener and the Fitzpatrick Chilsonator CCS220/M3B & RV-M5A with Screener Sweco Vibro-energy unit integrated under M5A. The compaction processing can be performed using two separate subsystems that are bound by a common electrical system. For example, a first subsystem (Roller Compactor: main unit) can be the Fitzpatrick Chilsonator CCS220 roller compactor and the M3B mill for pre-breaking the compacted material, while the second subsystem (Roller Compactor: secondary milling unit) is M5A mill for the final milling with a Sweco or Retch screener for the separation to obtain the desired size aggregates.

Humidified intermediate fine cellulosic fiber can be fed into the hopper of the roller compactor unit, first passed through a main milling unit and then proceed on through a second milling unit. A container can be provided that captures the pre-broken cellulosic material resulting from the main milling unit. The pre-broken pieces of cellulosic material can then be fed into the secondary milling unit, which performs the final milling and screening utilizing a screen mesh. The resulting milled cellulosic material is preferably separated into fines (<75 μm), targets (75-300 μm), and overs (>300 μm) using a screen mesh, such as the Sweco or Retch screener described above.

Referring to Table 3, testing showed that by using a lower size, as measured by d(50) and/or d(90), for the intermediate fine cellulosic fibers from the second milling step, resulted in aggregate product from the compactor sequence has spherical value that approaches 1. A higher fiber moisture content (16% LOD intermediate fine fibers as measured by Ohaus MB45 moisture analyzer resulted in resulting aggregates having a measured sphericity of 0.76. In contrast, when the moisture content for the intermediate fine fibers was around 11% LOD, the resulting aggregates had a sphericity of 0.72. Higher moisture content of intermediate ORC fibers results in higher sphericity of ORC compacted aggregates.

Preferred process parameters for the roller compaction and sieving processes are as follows: Roller Pressure about 125-135 bar, with target of 130 bar; Roller Speed about 3 RPM; Roller—diamond knurl; Starting material sizes are d50 less than about 95 microns and d90 less than 177 microns; Starting Moisture Content is greater than about 11% but less about 16%; Roll Force Values about 26.0 kN/cm; Horizontal feed screw speed about 19 rpm, vertical feed screw speed about 265 rpm; Sieving separated target hemostatic aggregates (d90 less than 370 microns, d50 between 140-242 microns and d15 higher than 86 microns. The preferred roller pressure is higher than levels typically used on roller compactors and produced materials having aggregate durability as demonstrated following vibratory challenge.

Cellulosic intermediate fine fiber batches were tested with different roller compaction systems. Of the tested systems, only the Fitzpatrick CCS20/M3B and IRR220-L1A models produced acceptable hemostatic aggregates. Without being held to any particular theory, it is believed that these preferred units were able to operate at sufficient roller force (26 kN/cm) and with a vertical orientation of the feed to the compaction rolls.

Moisture is removed from hemostatic aggregates that are obtained following roller compaction and sieving in a dehumidification or drying step. The dehumidification or drying step preferably does not significantly affect any other product quality attributes, such as color, bulk density, water soluble content, size, and sphericity. Typically, 750 grams or less of the powder can be dried as a batch using a conventional fluidized air bed. The resulting dried powder can be packed and stored in sealed foil pouches. Dehumidification equipment is known and commercially available. An exemplary bench-top fluidized air bed is commercially available from Retsch (TG-200) with 6 L capacity. Alternatively, a fluidized bed Model No. 0002 from Fluid Air (Aurora, Ill.) can also be used.

Example 1. Manufacturing and Characterization

Hemostatic aggregates were made from ORC material as described above through steps of slitting and cutting of ORC source material using SURGICEL® Original fabric including a first milling step, a second milling step via air classifier to obtain an intermediate fine ORC fiber, humidification of the intermediate fine ORC fiber, roller compaction, granulating, sieving and dehumidification.

Hemostatic aggregate materials comprise a plurality of individual fibrils of fine ORC fiber that have been compacted and joined together by a compaction process. In preferred aspects, the hemostatic aggregate materials comprise at least 5 elongated individual fibrils of fine ORC fiber, more preferably at least 10 elongated individual fibrils of fine ORC fiber, or between 5 and 100 elongated individual fibrils of fine ORC fiber, such as 10-50.

The resulting materials are aggregates, not particles. There is no core region or defined pores. Rather, the fibrils or fibers appear to form an interlocking web without loss of their fibril structure, each interconnected at discreet points. The processes described above produce aggregate having a fibril-interconnected structure with sufficient bulk to have connections and fibers to provide greater density than plasma, and strength to sink and then readily disperse to maximize the coagulating effects of the carboxylic groups.

Hemostatic aggregates of the present invention have an overall size (as determined by their largest dimension) of less than about 500 microns, but generally larger than about 50 microns. Hemostatic aggregate materials with such dimensions should comprise the majority of the particles constituting the final hemostatic material, i.e. over 50%, such as over 80% or over 90% of all particles. Preferred inventive hemostatic aggregate materials are characterized by a size distribution such that [d15>86 microns], [d50, 140–242 microns], [d90<370 microns] as measured by QICPIC FERET_MIN Q3 method. QICPIC is a high speed image analysis sensor available from Sympatec GMBH, Germany.

Bulk density is the ratio of the mass of an untapped powder sample and its volume including the contribution of the interparticulate void volume. Bulk density measurement was performed by following USP 616 (2012). Inventive hemostatic aggregate materials preferably have a bulk density (g/mL) within the range 0.3 to 0.7, preferably greater than 0.45 g/mL, such as 0.5 g/ml.

Sphericity (sh50) of the median particles (D50) was equal or greater than 0.5 by Sympatec QICPIC method, such as 0.70, where 1 corresponds to a sphere, indicating that the hemostatic aggregates have a relatively spherical shape. Sphericity was defined and measured as shown below. Sphericity of hemostatic aggregates is related to the diameter of a circle that has the same area as the projection area of the aggregate. The sphericity, S, is the ratio of the perimeter P of the equivalent circle, $P_{EQPC}$, to the real perimeter, $P_{real}$. For A=area of the particle, the sphericity is defined by the formula below:

$$S = \frac{P_{EQPC}}{P_{real}} = \frac{2\sqrt{\pi \cdot A}}{P_{real}}$$

The resulting sphericity has a value between 0 and 1. The smaller the value, the more irregular is the shape of the particle. This results from the fact that an irregular shape causes an increase of the perimeter. The ratio is always based on the perimeter of the equivalent circle because this is the smallest possible perimeter with a given projection area. The value of 1 corresponds to a perfect sphere.

Several sizes of hemostatic aggregate materials were developed and tested and compared to fine intermediate ORC fiber with differing particle size as shown in Table 1 below.

TABLE 1

Comparison of ORC based hemostatic powders and hemostatic aggregates tested.

| Name | Production | Size Range (sieve method, microns) | Bulk density | Observations |
|---|---|---|---|---|
| ORC Fine Fiber | Ball Milled or Hammer milled, shredding, no compaction | ORC Fine Fiber 1 (36.5 μm, d50 by DLS (Dynamic Light Scattering) ORC Fine Fiber 2 (62 μm, d50 by DLS) | 0.57 g/mL 0.43 g/mL | Too dusty, floats on blood and has poor efficacy |
| Hemostatic Aggregates Large | Hammer Milled, then roller compacted | 600 μm~800 μm | N/A | Good hemostasis efficacy, however granules are too large to spray, difficult to deploy onto the wound by spraying |
| Hemostatic Aggregates Coarse | Hammer milled or ball milled, then roller compacted | 106 μm~425 μm | 0.41 g/mL | Good hemostasis efficacy and ability to adhere to the wound site |
| Hemostatic Aggregates Fine | Hammer milled or ball milled, then roller compacted | 106 μm~300 μm | 0.37 g/mL | Good hemostasis efficacy and ability to adhere to the wound site |

If the compaction force is too low e.g. below about 10 kN/cm, the resulting material will return to its original state as a fine fiber in the granulator associated with the compaction system (post-compaction or secondary milling). If the compaction force is too high, the product will be "overpressed". Overpressing was observed when the material comes out of the roller compaction process, such as discolored extremely hot, or severely cracked. When using process parameters as defined above and using a vertical screw speeds of higher than 22 rpm, the compacted ribbon showed signs of burning, thereby thermally damaging the cellulosic material.

As described above, hemostatic aggregates are created by forcing ORC fine powder particles under pressure between two-counter rotating rolls to produce ribbon-like "compacts" that are then milled into aggregates, which are subjected to sieving to obtain desired hemostatic aggregates between 106 μm and 300 μm by screen sieving.

Again, without intending to be bound to any particular theory, the bonding mechanisms that may hold the particles together are (1) van der Waals' forces—during compaction, the ORC material is squeezed so that these van der Waals' forces bind all the material together to form a solid compacted aggregates and (2) and inter-molecular hydrogen bonding to bring all the material together as well when certain level of moisture is present.

Example 2

Using the manufacturing techniques explained above, hemostatic aggregate samples were prepared with and without humidification step; all other processing steps being equal. Both specimens were exposed to size distribution measurement by using Sympatec QICPIC equipment using 0.2 bar vacuum processing, and the size distribution curves were obtained (FIG. 1). Curve 1 shows size distribution of the specimen made with a humidification step applied to ORC intermediate fine fiber prior to roller compaction, while curve 2 shows size distribution of the specimen that was made without the humidification applied to ORC intermediate fine fiber.

After that both specimens 1 and 2 were exposed to a vibratory test. The test consisted of positioning vials containing 2 g of hemostatic aggregates powder on a sieve shaker (Retch AS200) which vibrated at amplitude of 1 mm/g for 90 minutes, followed by 3 mm/g for 90 minutes. After the vibratory challenge the specimens were again exposed to the same size distribution measurement by Sympatec QICPIC. The results are also shown in FIG. 2.

Figure 2:
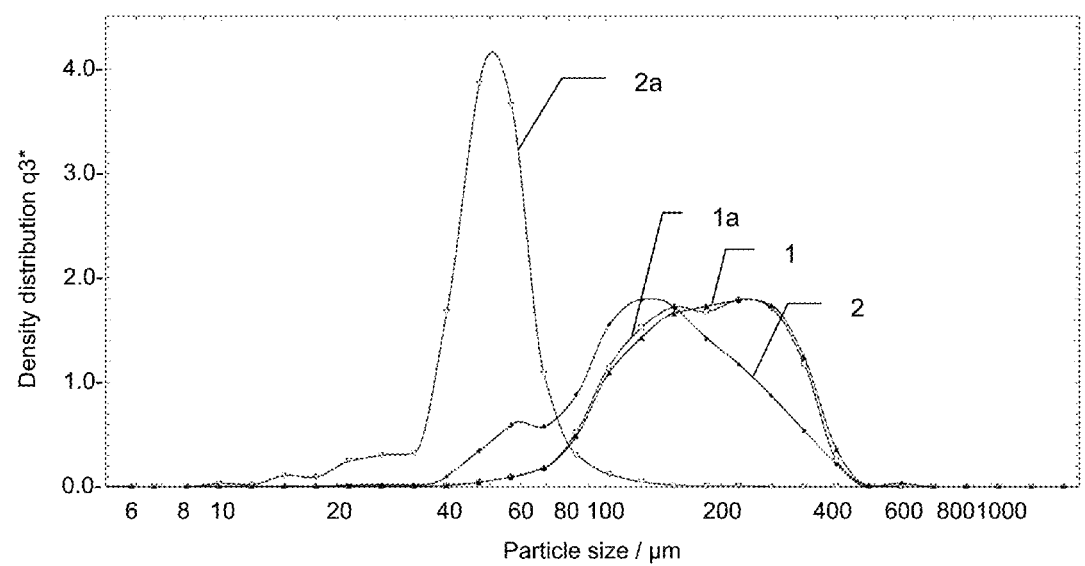
FIG. 2 is a graph showing a series of size distribution curves.

Curve 1a of FIG. 2 shows size distribution of the specimen made with a humidification step and exposed to a vibratory test. Curve 2a of FIG. 2 shows size distribution of the specimen made with no humidification step and exposed to the same vibratory test. It can be seen that the control specimen 2 which was made of ORC intermediate fine fiber not subject to humidification prior to roller compaction exhibited a significant change in size distribution from which the size decreased indicating breakage of the hemostatic aggregates into smaller subunits, with d50 changing from 137 microns to 50 microns. On the contrary, specimen 1 shows no appreciable change as curves 1 and 1a are very similar. The moisture content of humidified ORC intermediate fine fiber used to make hemostatic aggregates specimens having size distributions shown in curves 1 and 1a was within 11-16%. The moisture content of ORC intermediate fine fiber used to make hemostatic aggregates specimens shown in curves 2 and 2a was 2.0%. The significant change in properties as a result of the vibratory challenge is undesirable and may result in adverse effect on therapeutic efficacy, as will be shown below. The vibratory challenge indicates dosing, storage and transportation challenges that hemostatic aggregates can be subjected to in use, and thus a significant change in properties can result, with detrimental effect upon hemostatic efficacy. Advantageously, according to one aspect of the present invention, hemostatic aggregates have substantially no size distribution changes or minimal size distribution changes after subjected to a vibratory challenge, as measured by Sympatec QICPIC optical sensor at 0.2 bars.

Example 3

Figure 3:
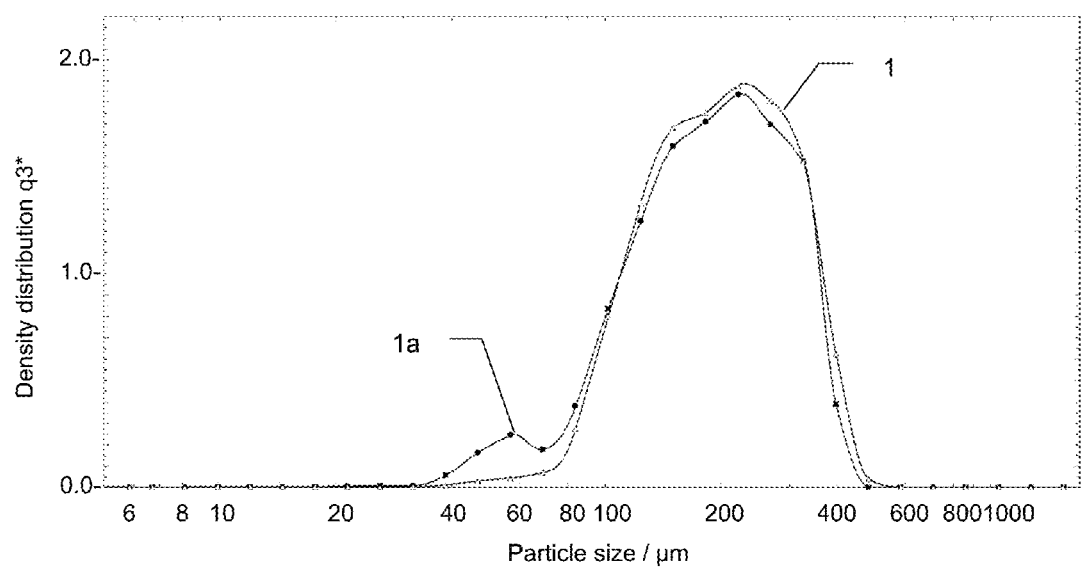
FIG. 3 is a graph showing a series of size distribution curves.

A test was performed using the methodology described above for size distribution measurements. As above, hemostatic aggregates samples prepared with and without humidification step, with all other processing steps being equal, were measured on the same QICPIC equipment but using two pressure settings—low pressure of 0.2 bar vacuum, and elevated pressure of 1 bar vacuum. Each specimen was exposed to size distribution measurement by using QICPIC equipment both 0.2 bar and 1.0 bar vacuum processing, and the size distribution curves were obtained for comparison. FIG. 3 shows curve 1 corresponding to size distribution measured at 0.2 bar for a hemostatic aggregates specimen made with a humidification step applied to ORC intermediate fine fiber prior to roller compaction. Curve 1a shows size distribution measured at 1.0 bar for the same hemostatic aggregates specimen. The data indicates that elevated processing pressure at 1.0 bar vacuum results in substantially the same size distribution or in minimal changes to size distribution for hemostatic aggregates specimen made with a humidification step applied to ORC intermediate fine fiber prior to roller compaction. d50 has varied from 190 to 199 microns only.

Figure 4:
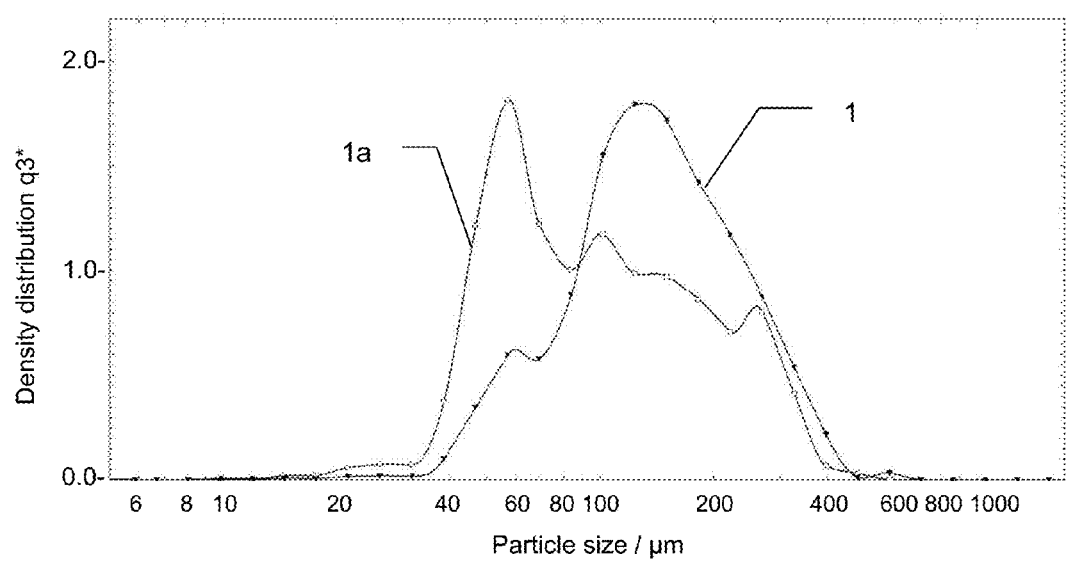
FIG. 4 is a graph showing a series of size distribution curves.

FIG. 4 shows the same testing performed for specimens manufactured without humidification step. FIG. 4 shows curve 1 corresponding to size distribution measured at 0.2 bar for an hemostatic aggregates specimen made without humidification step applied to ORC intermediate fine fiber prior to roller compaction. Curve 1a shows size distribution measured at 1.0 bar for the same hemostatic aggregates specimen. The data indicates that elevated processing pressure at 1.0 bar vacuum results in substantial change in size distribution for hemostatic aggregates specimen made no humidification step applied to ORC intermediate fine fiber prior to roller compaction. d50 has substantially changed from 147 to 84 microns indicating that the size of hemostatic aggregates shown in FIG. 4 is severely diminished when the pressure is increased.

High pressure treatment challenge can be related to hemostatic aggregates delivery via various delivery devices, including gas-assisted delivery. Advantageously, according to one aspect of the present invention, hemostatic aggregates have substantially no change in size distribution when subject to processing at 1.0 bar vacuum. Importantly, excessive mechanical agitation or collisional forces can detrimentally affect the hemostatic aggregates size distribution and thus affect the hemostatic efficacy. The collisional forces generated in a Sympatec QICPIC experiment is indicative of the sensitivity of hemostatic aggregates to pressure and can be used to qualitatively determine relative stabilities.

Example 4. Hemostatic Properties

In another aspect of the present invention, the hemostatic aggregates are shown to have superior hemostatic or blood clotting properties when tested in-vitro. Using the manufacturing techniques explained above, hemostatic aggregates samples were prepared with and without humidification step, with all other processing steps being equal. Some specimens were the also subjected to the vibratory challenge as described above.

Fresh porcine blood was placed in several 4.5 mL test tubes (BD Vacutainer) with a 3.2% buffered sodium citrate solution and diluted with saline solution (0.9% NaCl USP) with a ratio of 2.5/1 (v/v). 1 mL of this blood solution was then placed into a 7 mL glass vial followed by the application of 100 mg of each hemostatic aggregates sample and let standing for 2 minutes prior to evaluation. The vial was then flipped up-side-down allowing any non-clotted blood to exit the vial into a collecting receptacle. The remaining residues and clotted blood in each vial were then evaluated by weight. Each sample was tested in triplicate. The results are shown in Table 2.

TABLE 2

| Specimen | % remaining in vial | | | | OBSERVATIONS |
| | Test I | Test II | Test III | AVG. | |
| --- | --- | --- | --- | --- | --- |
| Control: No hemostatic aggregates added(blood only) | 5.43 | 4.38 | 2.70 | 4.17 | No clotting |
| hemostatic aggregates specimen made with a humidification step applied to ORC intermediate fine fiber prior to roller compaction | 98.21 | 95.77 | 97.38 | 97.12 | Excellent clotting |

TABLE 2-continued

| Specimen | % remaining in vial | | | | OBSERVATIONS |
| | Test I | Test II | Test III | AVG. | |
| --- | --- | --- | --- | --- | --- |
| hemostatic aggregates specimen made with a humidification step applied to ORC intermediate fine fiber prior to roller compaction, then subjected to vibratory challenge | 97.05 | 91.97 | 93.64 | 94.22 | Excellent clotting After vibration |
| hemostatic aggregates specimen made with no humidification step | 98.82 | 97.14 | 94.58 | 96.85 | Excellent clotting |
| hemostatic aggregates specimen made with no humidification step, then subjected to vibratory challenge | 14.30 | 15.38 | 12.88 | 14.19 | Poor clotting After vibration |

Analysis of data indicates that hemostatic aggregates specimens made with a humidification step applied to ORC intermediate fine fiber prior to roller compaction exhibited excellent in vitro blood clotting, even after subjected to the vibratory challenge. On the contrary, while hemostatic aggregates specimen made with no humidification step exhibited excellent in vitro blood clotting, the same specimen after being subjected to the vibratory challenge exhibited poor in vitro clotting. According to one aspect of the present invention, mechanical stability of hemostatic aggregates results in sustained hemostatic properties.

Example 5

Referring to Table 3, showing parameters of hemostatic aggregates obtained in different batches, with parameters reported as averages of three tests. Process parameters were similar, with different feeding material (intermediate fine fiber). Blood clotting was measured using methods described above. Bulk density and size distributions of hemostatic aggregates were measured using methods described above.

As can be seen from Table 3, good clotting is achieved for hemostatic aggregates having a value of sphericity (sh50) equal of higher than about 0.6. The best clotting, i.e. with over 80% of blood remaining in vial, was achieved for hemostatic aggregates having a value for its sphericity (sh50) of at least about 0.7 and a bulk density above 0.5 (g/ml). It is noted that smaller sizes of feeding material resulted in hemostatic aggregates having these properties. Analysis of data indicates that hemostatic aggregates specimens made with a humidification step applied to ORC intermediate fine fiber prior to roller compaction and having bulk density above 0.5 exhibited excellent in vitro blood clotting. Analysis of data further indicates that hemostatic aggregates specimens made with a humidification step applied to ORC intermediate fine fiber prior to roller compaction and having sphericity (sh50) above 0.7 exhibited excellent in vitro blood clotting.

Based on the data in Table 3, hemostatic aggregates of the present invention have average sphericity above 0.6, preferably above 0.65, more preferably above 0.7, most preferably above 0.75.

TABLE 3

| Batch | Avg % (blood remaining) | Avg. Sphericity | Avg. Bulk Density (g/ml) | d(15) (microns) | d(50) (microns) | d(90) (microns) | (Int. Fine Fiber) [d50, d90, microns] |
|---|---|---|---|---|---|---|---|
| Control | 5.51 | N/A | | | | | |
| A | 30.64 | 0.56 | 0.321 | 118 | 221 | 372 | [128, 271] |
| B | 59.81 | 0.59 | 0.331 | 113 | 203 | 357 | [133, 268] |
| C | 63.16 | 0.61 | 0.365 | 132 | 228 | 368 | |
| D | 71.61 | 0.67 | 0.423 | 85 | 178 | 328 | [96, 200] |
| E | 85.45 | 0.73 | 0.510 | 121 | 206 | 340 | |
| F | 96.80 | 0.76 | 0.525 | 111 | 178 | 307 | |
| G | 96.71 | 0.79 | 0.528 | 145 | 209 | 320 | [65, 122] |

Note: for line G material, the intermediate fine fiber was made using the ball mill process. Ball milling method to convert fabric to intermediate ORC fine fibers is described as the follows. 50 g of pre-cut ORC fabric (2"×2") was ball milled with 12 high-density Zirconia balls 20 mm in diameter (Glen Mills Inc., Clifton, N.J., USA) by placing the balls and the samples in a 500 mL grinding jar. The jar was clamped into latching brackets and then counterbalanced on a planetary ball mill PM100 (Retsch, Inc., Newtown, Pa., USA). The milling was then performed bi-directionally at 450 rpm for 20 minutes.

A linear regression and plot can be generated for d(50) [y=−301.03x+301.92, where $R^2$ is 0.950] and d(90) [y=−680.11x−659.02, where $R^2$ is 0.9887] for the source intermediate fine fiber relative to the resulting hemostatic aggregates sphericity. Finer intermediate fine fiber results in higher sphericity of hemostatic aggregates, such as with intermediate fine powder having d(50) about 65 microns and d(90) about 120 microns, the sphericity of hemostatic aggregates is about 0.8. The same correlations are seen in Table 3.

As shown in Table 3, for d(50) and d(90) of intermediate fine powder being 96 and higher (i.e. 96 to about 130 for d(50) and 200 to about 270 for d(90), the resulting blood clotting was 70%-30% and the sphericity was 0.56-0.67. For d(50) and d(90) of intermediate fine powder being lower than 96 (i.e. 35 for d(50)) and lower than 200 (i.e. 122 for d(90)), the resulting blood clotting was above 80% and the sphericity was above 0.7. Smooth edged hemostatic aggregates, especially those having a sphericity that approaches 1, flow well in applicator or sprayer, while spikey hemostatic aggregates flowed less-well in applicator.

Figure 5:
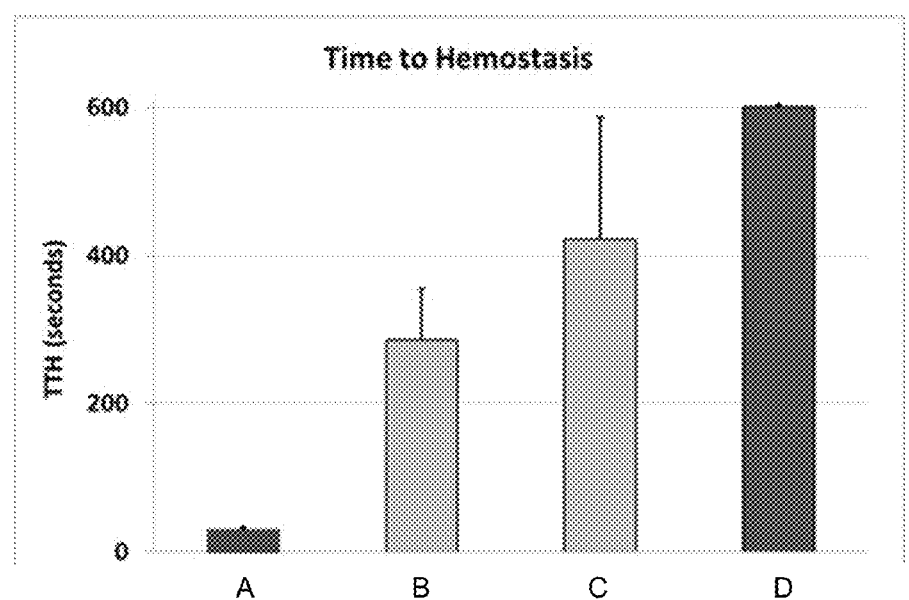
FIG. 5 is a graph showing performance of selected materials.

Referring now to FIG. 5, the results of hemostatic testing of the hemostatic aggregates shown in comparison with other hemostatic materials. A swine punch biopsy liver defect model was used. The test materials were hemostatic aggregates (referenced as bar A on the chart); plant based absorbable microporous polysaccharide hemostatic powder derived from purified plant starch (referenced as bar B); and plant starch powder forming hydrophilic, adhesive hemostatic polymers consisting of absorbable polysaccharides (referenced as bar C on the chart).

Test Method: 6-mm diameter by 3-mm deep defects were created using a biopsy punch. The site was allowed to bleed for several seconds prior to product application. The defect trial site was scored as hemostatic (Pass) if hemostasis was achieved in ≤10 minutes and maintained for 1 minute without occlusive pressure, non-hemostatic sites were scored "Fail". Time to Hemostasis (TTH) was measured for Pass sites. As can be seen from the FIG. 5, hemostatic aggregates produced a significantly lower TTH than comparative materials, 89% faster TTH than material B, and 93% faster TTH than material C with a p-value <0.001 in both cases. Bar D on the chart corresponds to negative control, i.e. bleeding where no hemostatic agent was applied.

Example 6

Particle size distributions were obtained for the ORC aggregates and fine fibers. A typical aggregate material had volume weighted Feret Minimum D(15), D(50), and D(90) values of 111, 178, and 307 microns. This powder also had a sphericity, Sh(50)=0.76. Typical ORC fine fibers had length weighted fiber length D(10), D(50), and D(90) values of 30, 72, and 128 microns.

Particle sizes and shapes were obtained with a Sympatec QICPIC image analyzer (Sympatec GMBH, Clausthal-Zellerfield, Germany). It has a camera resolution of 1024× 1024 pixels with a pixel size of 10×10 $\mu m^2$. Its measurement range is from 5 to 1705 μm. A VIBRI/L vibratory feeder was used to introduce solid particles into a RODOS/L disperser. Images of the dispersed particles were then obtained in the QICPIC with a camera frame rate of 450 fps. A Feret min Q3 method was used to calculate the particle sizes of the aggregates while a Sympatec LEFI Q1 algorithm was used to determine the fiber lengths of the fibers.

The sphericity [Sh(50)] of the median-diameter aggregates was determined by the Sympatec QICPIC method using the ratio of the perimeter P of the equivalent circle ($P_{EQPC}$) to the real perimeter ($P_{real}$), in which A=area of the particle, shown in the equation $S=(P_{EQPC})/(P_{real})= 2(\pi A)^{1/2}/(P_{real})$. The area of the equivalent projection circle has the same area as the projection area of the real particle.

Surface Area and Surface Wettability

Further characterizations of the materials were performed measuring surface area and wettability of each hemostatic material. Wettability provides a relative measure of surface polarity, and therefore the extent of hydrophilic or hydrophobic behavior of a material with whole blood. Surface area analyses were performed with inverse gas chromatography (Surface Measurement Systems Model IGC-SEA, Alperton, UK). Approximately 750 mg of each sample was packed into individual silanized glass columns (300 mm long by 4-mm inner diameter). Each column was conditioned with helium gas for 60 minutes at 37° C. and 0% relative humidity. All experiments were conducted at 37° C., with 10 mL/min total flow rate of helium, using methane for dead volume corrections. The Brunauer, Emmett, and Teller (BET) model was used for surface area determinations, based on sorption isotherms with HPLC-grade decane (Sigma-Aldrich, St Louis, Mo., USA) using the chromatograph in pulse sorption method.

The Brunauer, Emmett, and Teller (BET) surface areas for ORC aggregates [Sh(50)=0.76], ORC aggregates [Sh(50)=0.51], ORC fine fibers, and starch based spheres are shown in Table 4. ORC aggregates with sphericity values of 0.51 and 0.76 had surface areas of 0.67 $m^2/g$ and 0.40 $m^2/g$, respectively. ORC aggregates and fine fibers belong to the same family of oxidized regenerated cellulose but ORC aggregates had a lower surface area/mass ratio. It was also found that ORC aggregates with lower sphericity values had higher surface areas than aggregates with higher sphericity values if they had similar particle size distributions. In contrast to the ORC powders, the starch-based spheres had the highest surface area of the four materials.

TABLE 4

Sphericity and Surface Area of Test Materials

| Test material | Sphericity Sh(50) | Surface Area $m^2/g$ |
|---|---|---|
| ORC aggregates | 0.76 | 0.40 |
| ORC aggregates | 0.51 | 0.67 |
| ORC fine fibers | N.A. | 1.17 |
| Starch-based spheres | 0.93 | 2.03 |

Analysis of Table 4 indicates that ORC aggregates with high sphericity values had much lower surface area vs. ORC fine fibers and ORC aggregates of low sphericity. ORC aggregates with high sphericity had surface area 1.5 times lower vs. ORC aggregates of low sphericity and close to 3 times lower vs. ORC fine fiber.

The wettability or hydrophilicity of the test materials was determined by dividing the acid-base surface energy by the total surface energy ($\gamma^{AB}/\gamma^T$). The surface energy profile was determined by mapping techniques in which the specific free energies of desorption were determined by polarization. The dispersive surface energy component ($\gamma^D$) was measured by the method of Dorris and Gray using nonpolar HPLC grade probes: decane, nonane, octane, and heptane (Sigma-Aldrich, St Louis, Mo., USA). The acid-base surface energy component ($\gamma_s^{AB}$) was determined using the Good-van Oss-Chaudhury (GvOC) model, in which the acid-base component is taken as the geometric mean of the Lewis acid parameter ($\gamma_s^-$) and Lewis base parameter ($\gamma_s^+$). The total surface energy ($\gamma^T$) is the sum of the dispersive surface energy and the acid-base surface energy ($\gamma^T=\gamma^D+\gamma_s^{AB}$). Because $\gamma_{blood}^{AB}$ values were not available, the above equations were simplified to calculate the works of adhesion and cohesion from the total surface energy values only, using the surface tension value for blood ($\gamma_{blood}^T$) at 37° C.=52.6 $mJ/m^2$. The surface wettability results are presented in Table 5.

TABLE 5

Surface wettability

|  | Surface Wettability |
|---|---|
| ORC Aggregates Sh(50) = 0.76 | 0.0384 |
| ORC Aggregates Sh(50) = 0.51 | 0.0746 |
| ORC Fine Fibers | 0.110 |
| Starch-based Spheres | 0.130 |

Analysis of Table 5 indicates that ORC aggregates with high sphericity values had much lower wettability vs. ORC fine fibers and ORC aggregates of low sphericity. ORC aggregates with high sphericity had wettability almost 2 times lower vs. ORC aggregates of low sphericity and close to 3 times lower vs. ORC fine fiber.

Density

The "true density" of the materials was obtained by the gas pycnometer. The results are presented in Table 6. While densities of ORC materials and starch spheres tested are all higher than water density of 1.0 g/cm3, it is observed that interactions with blood were different. Only the aggregates of high sphericity have immediately penetrated the blood surface and initiated rapid clotting. Lower sphericity aggregates as well as fine ORC fibers predominantly or partially stayed on the surface of blood as will be discussed below. In fact the true densities of all tested ORC aggregates and fine fibers are close, but high sphericity ORC aggregates exhibited immediate penetration of the blood surface.

TABLE 6

True Density of tested materials

| Material | Density (g/cm3) |
|---|---|
| Starch-based Spheres sample 1 | 1.3009 |
| Starch-based Spheres sample 2 | 1.2987 |
| Starch-based Spheres sample 3 | 1.299 |
| Low sphericity ORC aggregate sample 1 | 1.5457 |
| Low sphericity ORC aggregate sample 2 | 1.5451 |
| Low sphericity ORC aggregate sample 3 | 1.5451 |
| ORC Fine Fiber sample 1 | 1.5313 |
| ORC Fine Fiber sample 2 | 1.5316 |
| ORC Fine Fiber sample 3 | 1.5313 |
| High sphericity (0.76) ORC aggregate sample 1 | 1.5874 |
| High sphericity (0.76) ORC aggregate sample 2 | 1.5875 |
| High sphericity (0.76) ORC aggregate sample 3 | 1.5873 |

Despite similar density, ORC materials exhibited surprisingly different patterns of interactions with blood. The ORC fine fibers primarily floated on the surface of the blood with little penetration. The ORC low sphericity aggregates exhibited some penetration but not as deep as the high sphericity aggregates.

The ability to penetrate into the blood appears to be directly related to the surface areas of the ORC materials. Higher surface area resulted in less penetration. Lower surface area materials will sink more rapidly into the blood. Wettability is another distinguishing feature of these three materials. The ORC fine fibers and low sphericity aggregates have slightly higher wettability values than that of high sphericity aggregates. They are more hydrophilic. Powders with high surface areas and wettability values will interact with blood more rapidly than those with low surface areas and wettability values. Since the rate of gelation of ORC and blood is relatively fast, powders with higher surface areas and wettability are not able to penetrate into the blood and will remain near the surface. On the other hand, lower surface area powders with low wettability will be able to interact with a larger volume of blood, resulting in better clots.

The starch based spheres have the highest surface area of all the materials and their degree of penetration into blood was minimal.

Example 7. In Vitro Clotting. Further Hemostatic Evaluations

Fresh porcine blood was collected in 4.5-mL Vacutainer tubes (Becton, Dickinson and Company, Franklin Lakes, N.J., USA), with a 3.2% buffered sodium citrate solution. A 1-mL aliquot of diluted blood was then transferred to a 7-mL vial, after which 100 mg of each test article was applied.

Clotting was allowed to proceed for 2 minutes at room temperature. The vial was capped, flipped upside down and placed on a tapped density analyzer (Quantachrome Autotap EC148; Quantachrome Instruments, Boynton Beach, Fla., USA) and tapped mechanically 5 times. After 2 minutes the cap was removed, unclotted material drained by gravity, and the remaining residue in each vial was calculated by weight. Six replicates were performed for each sample.

The hemostatic activity of the ORC aggregates prepared at 2 sphericity values [Sh(50)=0.51 and Sh(50)=0.76], the ORC fine fibers from which the aggregates were derived, and a commercially available hemostat composed of starch-based spheres were examined. This investigation was initiated to determine how overall sphericity of the ORC test materials affected clotting and how these experimental products compared with an approved absorbable hemostat.

Samples were evaluated prior to and through up to 2 minutes after addition of 100 mg of each hemostat. In each panel, tube #1 was an untreated control, tube #2 was treated with starch-based spheres, tube #3 was treated with ORC fine fibers, tube #4 was treated with low sphericity ORC aggregates [Sh(50)=0.51], and tube #5 was treated with high sphericity ORC aggregates [Sh(50)=0.76].

It was observed that within seconds there were visible differences in the activity of the test materials. The ORC aggregates with high sphericity [Sh(50)=0.76] immediately penetrated the surface of the blood and initiated coagulation. The ORC aggregates with less sphericity [Sh(50)=0.51] penetrated, but to a lesser extent; and the ORC fine fibers (essentially aspherical) remained somewhat superficial on the surface of the liquid blood. The starch-based spheres remained on top of the blood surface and did not penetrate into the liquid. This indicated that a high degree of sphericity contributed to the blood-penetrating properties of ORC aggregates. However, sphericity itself was not the only factor affecting penetration, as the starch-based spheres were the least penetrating and most spherical material tested [Sh(50)=0.93].

At 2 minutes there were visible differences in the clotting activity of the test materials. All the blood in the vial treated with high sphericity ORC aggregates was fully clotted, evidenced by the dark reddish-black color that is characteristic of ORC clots. The blood treated with low sphericity ORC aggregates and ORC fine fibers appeared less involved, and the blood treated with starch-based spheres appeared about the same as untreated control blood. When the vials were inverted, only the high sphericity ORC aggregates appeared to produce a robust, adherent clot. There was no coagulation in the control tube containing untreated blood. The high sphericity ORC aggregates produced a fully involved clot that adhered to the vial. The low sphericity ORC aggregates produced a less adherent clot, and the ORC fine fibers produced a modest clot. There was almost no clot in the tube treated with starch-based spheres.

Figure 6:
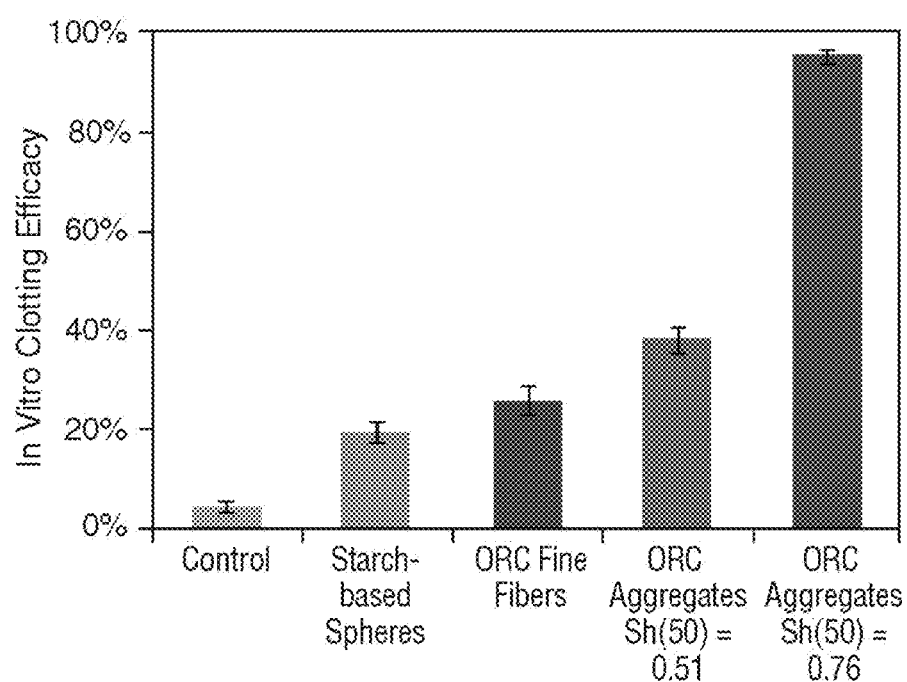
FIG. 6 is a graph showing performance of selected materials

The clotting efficacy was quantified by comparing the mass of the blood in the vials before and after inversion. Vials were inverted, mechanically tapped 5 times with a tapped density analyzer, and allowed to rest for 2 minutes; unclotted blood simply dripped out from the bottom of the vial, and the remaining residue in each vial was calculated by weight; each sample was tested in 6 replicates. The results of this testing are shown in FIG. 6. The clotting efficacy for the high and low sphericity ORC aggregates was 95% and 38%, respectively. The clotting efficacy for ORC fine fibers and starch-based spheres was 26% and 19%, respectively. Untreated blood only retained 4% of its weight as a clot. Error bars are ±standard deviation. High sphericity ORC aggregates had the greatest clotting efficacy.

Figure 7:
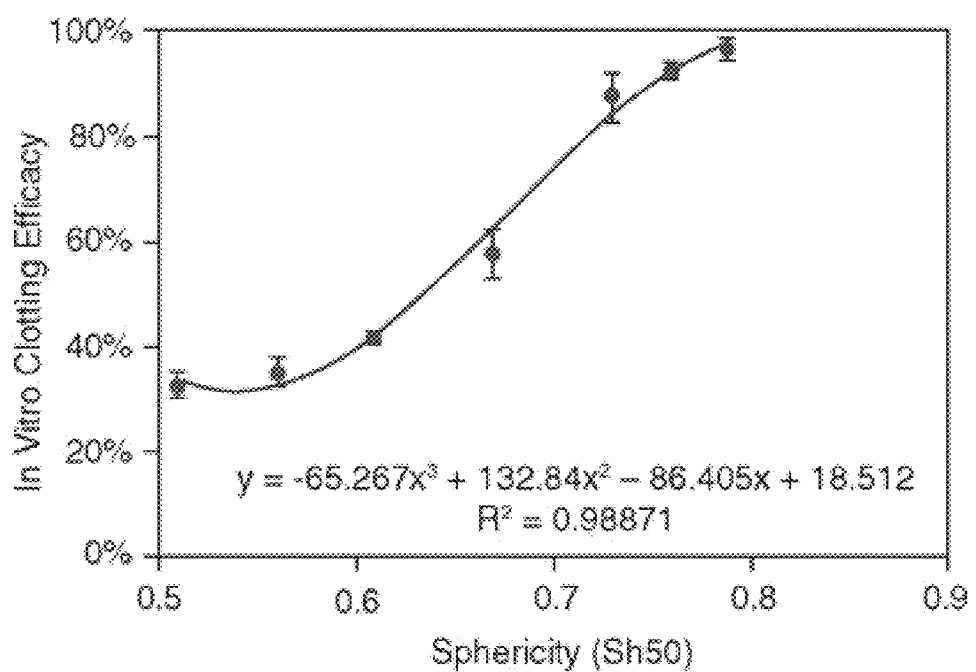
FIG. 7 is a graph showing performance of selected materials

Example 8. In Vitro Clotting. Effect of Aggregate Sphericity on Coagulation Efficacy Aggregates with several different sphericity values were produced and compared. Comparing aggregates with similar particle size distribution, more spherical aggregates had a smaller surface area and had the highest clotting efficacy. In vitro coagulation assays were performed on batches of ORC aggregates with sphericity values ranging from 0.51 to 0.79. The results are presented in FIG. 7, indicating that more spherical aggregates had greater clotting efficacy than less spherical forms. At a sphericity of 0.79, clotting efficacy was nearly 96%, whereas at a sphericity of 0.51 the efficacy was less than 33%. Error bars are ±standard deviation. Sphericity over 0.65, more preferably over 0.70, most preferably over 0.75 is preferred for high efficacy clotting.

Example 9. In Vivo Hemostasis

A long-term stability study that evaluated the effects of storage conditions and accelerated aging on hemostatic performance in a liver punch biopsy model in swine was conducted. Within the larger study, it was possible to compare the effect of ORC aggregate sphericity [Sh(50)=0.56 or Sh(50)=0.76] on hemostatic efficacy.

This study used five female Yorkshire Cross pigs weighing 54 to 57 kg. Biopsy punch defects were created using a 6-mm biopsy punch device marked to a depth stop of approximately 3 mm with surgical tape. A biopsy punch was used to incise the parenchymal surface of the liver at an angle perpendicular to the tissue using a gentle twisting motion. Once the tissue was incised to the required 3-mm depth, the punch was removed. The tissue in the center of the punch site was removed using forceps and surgical scissors and the assigned treatment was applied.

After a trial biopsy punch site was created, it was blotted with gauze and the appropriate test article was applied to the site. A dry nonadherent wound dressing (e.g., Telfa™ Non-Adherent Dressing) was applied on top of the test material followed by digital pressure ensuring that adequate and even tamponade was applied to the site.

Pressure was initially held for 30 seconds followed by removal of the nonadherent dressing and a 30-second evaluation for hemostasis. When bleeding occurred during the initial evaluation period, pressure was immediately reapplied using a nonadherent wound dressing for an additional 30 seconds followed by another 30-second evaluation for hemostasis up to a total time of 2 minutes after product application. When bleeding did not occur within the 30-second observation period, the time to hemostasis was noted as the time when the last applied tamponade was released. Any site that achieved hemostasis within 2 minutes was then lavaged with up to 10 mL of saline and observed for durable (maintained) hemostasis over another 30-second observation period. If bleeding occurred following lavage, durable hemostasis was noted as "fail," and the surgeon used remedial measures to control bleeding before continuing with the testing period. If hemostasis was maintained during the 30-second observation period following lavage, durable hemostasis was noted as "pass." If during the testing period tamponade and observation periods continued longer than 2 minutes, i.e., hemostasis was not achieved, the site was aborted and time to hemostasis was recorded as more than 2 minutes in the raw data. This occurred only at negative control sites. This procedure was repeated with each test article as indicated. There was no attempt to reapply an article if there was a failure to achieve hemostasis when the article was applied successfully. Negative control sites were untreated.

The differences in in vivo hemostatic efficacy with regard to sphericity were observable that paralleled the in vitro coagulation results. All sites treated with ORC aggregates [Sh(50)=0.56, n=16; Sh(50)=0.76, n=12] had a median time to hemostasis of 30 seconds, and 100% of sites were fully hemostatic within 2 minutes. However, 38% of sites treated with low sphericity ORC aggregates had delayed bleeding, necessitating remedial application of another ORC material (ORC snow) to control significant hemorrhage that occurred after the sample had been tested and classified as successfully hemostatic.

These observations confirmed in vitro data indicating that the aggregates with greater sphericity were more effective hemostatic agents.

In further aspects of the present invention, the hemostatic aggregates can be combined with various additives to further improve the hemostatic properties, wound healing properties, and handling properties, utilizing additives known to these skilled in the art, including: hemostatic additives, such as gelatin, collagen, cellulose, chitosan, polysaccharides, starch, CMC, calcium salts; biologics based hemostatic agents as exemplified by thrombin, fibrinogen, and fibrin; additional biologics hemostatic agents include, without limitation, procoagulant enzymes, proteins and peptides, each such agent can be naturally occurring, recombinant, or synthetic, and may be further selected from the group consisting of fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, albumin, platelet surface glycoproteins, vasopressin and vasopressin analogs, epinephrine, selectin, procoagulant venom, plasminogen activator inhibitor, platelet activating agents, synthetic peptides having hemostatic activity, derivatives of the above and any combination thereof. Preferred biologic hemostatic agents that can used in combination with the ball-milled ORC particles are thrombin, fibrinogen and fibrin; Anti-infective agents, such as chlorhexidine gluconate (CHG), triclosan, silver, and similar anti-bacterial/microbial agents that are known in the art; and additives that increase the stickiness of the hemostat; diluents, saline solutions, and similar additives that known in the art.

Having shown and described various versions in the present disclosure, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

I claim:

1. A method of making a plurality of hemostatic aggregates comprising the steps of:
   a) milling a cellulosic source material to form fibers;
   b) humidifying the fibers to water content of between 11.0% and 20% by weight;
   c) roller compacting the fibers to form hemostatic aggregates;
   d) sieving the hemostatic aggregates;
   e) dehumidifying the hemostatic aggregates to a moisture content of less than 5.5% determined by loss on drying; and
   f) optionally dosing the resulting hemostatic aggregates into storage containers or into delivery devices.

2. The method of claim 1, wherein, the step a) is preceded by a step of slitting and cutting the cellulosic source material forming pieces acceptable for milling in step a).

3. The method of claim 2, wherein, the step a) is a two-part process with the second part performed in an air classifier or ball mill process.

4. The method of claim 3, wherein the second part is repeated three times.

5. The method of claim 4, wherein the fibers have a size distribution of d50 less than about 100 microns and d90 of less than about 180 microns.

6. The method of claim 1, wherein said step c) is performed by compacting the fibers into a compacted material which is then subjected to pre-breaking, followed by a step of final milling.

7. The method of claim 6, wherein said compacting of the fibers is performed at a roller pressure of at least 125 bars.

8. The method of claim 6, wherein said compacting the fibers is performed at a roller force of at least 26.0 kN/cm.

9. The method of claim 1, wherein said step d) is performed to select a targeted hemostatic aggregates fraction having dimensions of 75-300 μm by screen sieving.

10. The method of claim 1, wherein said step d) is performed to select a targeted hemostatic aggregates fraction characterized by a size distribution such that d15 greater than or equal to ≥80 microns, d50 is from 140 to 250 microns and d90 less than or equal to ≤370 microns.

11. The method of claim 1, wherein said step e) is performed to hemostatic aggregates having moisture content of less than 2% determined by loss on drying.

12. The method of claim 1 wherein the source material is oxidized regenerated cellulosic fabric, oxidized regenerated cellulose non-woven fabric, shredded oxidized regenerated cellulosic material or combinations thereof.

13. The method of claim 1 wherein the source material further comprises an additive selected from the group consisting of carboxymethyl cellulose, calcium salt, an anti-infective agent, a hemostasis promoting agent, gelatin, collagen, of and combinations thereof.

14. The method of claim 1 further comprising a step of admixing an additive prior to step a), or prior to step b) by admixing the additive to the fibers; or prior to step c) by admixing the additive to the humidified fibers; or prior to step e) by admixing the additive to the hemostatic aggregates prior to drying or prior to step f) by admixing the additive to the hemostatic aggregates prior to dosing.

* * * * *